United States Patent
Jonsen (10) Patent No.: US 7,689,278 B2
(45) Date of Patent: Mar. 30, 2010

(54) IDENTIFICATION SYSTEM FOR DEFIBRILLATOR ELECTRODE PACKAGE

(75) Inventor: Eric Jonsen, Seattle, WA (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 708 days.

(21) Appl. No.: 10/573,065

(22) PCT Filed: Sep. 7, 2004

(86) PCT No.: PCT/IB2004/051707

§ 371 (c)(1),
(2), (4) Date: Mar. 23, 2006

(87) PCT Pub. No.: WO2005/030327

PCT Pub. Date: Apr. 7, 2005

(65) Prior Publication Data

US 2007/0112389 A1 May 17, 2007

Related U.S. Application Data

(60) Provisional application No. 60/507,156, filed on Sep. 30, 2003.

(51) Int. Cl.
*A61N 1/39* (2006.01)
(52) U.S. Cl. ............................................. 607/5; 607/8
(58) Field of Classification Search .................. 607/5–6, 607/27, 122, 142; 320/107; 235/451
See application file for complete search history.

(56) References Cited

U.S. PATENT DOCUMENTS

| | | | |
|---|---|---|---|
| 4,553,026 A * | 11/1985 | Arlowe | 235/451 |
| 4,634,847 A * | 1/1987 | Jurgen | 235/451 |
| 5,607,454 A | 3/1997 | Cameron et al. | |
| 5,735,879 A | 4/1998 | Gliner et al. | |
| 5,951,598 A | 9/1999 | Harris et al. | |
| 5,989,053 A * | 11/1999 | Wheeler | 439/387 |
| 6,018,683 A * | 1/2000 | Verness et al. | 607/122 |
| 6,084,380 A * | 7/2000 | Burton | 320/107 |
| 6,101,413 A * | 8/2000 | Olson et al. | 607/5 |
| 6,125,298 A | 9/2000 | Gilman et al. | |
| 6,560,485 B2 * | 5/2003 | Herleikson | 607/27 |
| 6,961,611 B2 * | 11/2005 | Dupelle | 607/5 |
| 6,990,373 B2 * | 1/2006 | Jayne et al. | 607/5 |
| 7,016,726 B1 * | 3/2006 | Picardo et al. | 607/5 |
| 2002/0156503 A1 | 10/2002 | Powers et al. | |
| 2004/0162586 A1* | 8/2004 | Covey et al. | 607/5 |

FOREIGN PATENT DOCUMENTS

WO   WO 94/27674     12/1994
WO   WO 03/020362 A   3/2003

* cited by examiner

*Primary Examiner*—Carl H Layno
*Assistant Examiner*—Luther G Behringer
(74) *Attorney, Agent, or Firm*—W. Brinton Yorks, Jr.

(57) ABSTRACT

An automatic external defibrillator electrode package includes a coded conductive label that uniquely identifies the type of automatic electrode contained therein. Pins on the defibrillator body make electrical contact with the conductive label when the package is attached to the defibrillator. These pins sense the shape of the conductive label to ascertain the electrode type, thereby enabling the AED to automatically set the proper operating mode.

20 Claims, 6 Drawing Sheets

IDENTIFICATION SYSTEM FOR DEFIBRILLATOR ELECTRODE PACKAGE

CROSS REFERENCE TO RELATED APPLICATION

This application claims the benefit of U.S. provisional application Ser. No. 60/507,156 filed Sep. 30, 2003, which is incorporated herein.

The present invention relates generally to automatic external defibrillators, and more particularly to a method and apparatus for attaching electrodes in an automatic external defibrillator.

Present automatic external defibrillators (AEDs) must adapt their operation to the mode of use. For example, an AED may be used to defibrillate an adult or an infant, each of which requires a different treatment protocol. Moreover, an AED may also be used in a training mode or strictly in a multi-electrode monitoring mode, in which case no defibrillation energy should be discharged through the electrodes. Thus, an AED must employ some technique for determining the operating mode.

There are a number of ways that present AEDs switch operating modes. One way is via a manual switch. A user of the AED simply changes a switch setting to the proper mode. Manual switching represents a suboptimal solution because setting a manual switch requires a user who may be employing the AED in a cardiac emergency to perform an extra and potentially confusing step to ensure the AED is in the proper rescue mode. Placing the AED in the wrong operating mode can have fatal consequences in certain situations.

Another technique employed by existing AEDs uses a different plug for each type of electrode. In this case, the AED merely senses which electrode is in use. This solution is impractical because it adds complexity to a device that must be simple, small, inexpensive and lightweight.

One method of automatically identifying the type of connected electrode is described in U.S. Pat. No. 6,560,485 to Herleikson and assigned to the same assignee, which patent is entitled "Four Contact Identification Defibrillator Electrode System." This patent describes segmented male and female plugs that selectively short together the segments when the plugs are mated. This patent is hereby incorporated by reference as if repeated herein in its entirety, including the drawings.

The present invention is therefore directed to the problem of developing a method and apparatus for enabling activation of the proper operating mode for an automatic external defibrillator that does not increase the size, weight or complexity of the automatic external defibrillator.

The present invention solves these and other problems by providing an automatic external defibrillator electrode package that comprises a coded conductive label that uniquely identifies the type of automatic electrode contained therein. Pins on the defibrillator body make electrical contact with the metallic label when the package is attached to the defibrillator. These pins sense the shape of the conductive label to ascertain the electrode type, thereby enabling the AED to automatically set the proper operating mode.

According to one aspect of the present invention, an exemplary embodiment of a method for identifying an electrode type in an automatic external defibrillator includes providing a shaped conductive label on an automatic external defibrillator electrode package that uniquely identifies a type of electrode contained therein and coupling one or more pins to the shaped conductive label when the automatic external defibrillator electrode package is coupled to the defibrillator. In this embodiment, a shape of the shaped conductive label can be sensed with the one or more pins to ascertain the type of electrode contained therein and an operating mode for the automatic external defibrillator can be selected based on the shape of the shaped conductive label.

According to another aspect of the present invention, an electrode package for an automatic external defibrillator includes a cartridge and a shaped metallic label. The cartridge contains one or more electrodes of a particular type. The shaped metallic label is disposed on the cartridge and uniquely identifies the particular type of electrode contained therein via its shape.

According to still another aspect of the present invention, an automatic external defibrillator includes one or more electrode cartridges and one or more shaped metallic labels. Each of the one or more electrode cartridges contains one or more electrodes of a particular type. Each of the one or more shaped metallic labels is disposed on one of the one or more electrode cartridges and each uniquely identifies a particular type of electrode contained therein based on its shape. This embodiment can include an electrode cartridge receptacle to accept each of the one or more electrode cartridges. The electrode cartridge receptacle includes one or more sensing pins to couple in a unique pattern to the one or more shaped metallic labels when each of the one or more electrode cartridges is inserted into the electrode cartridge receptacle. Moreover, this embodiment can include a processor establishing a mode of operation of the automatic external defibrillator based on the particular one of the one or more shaped metallic labels sensed by the one or more sensing pins.

It is worthy to note that any reference herein to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

Figure 1:
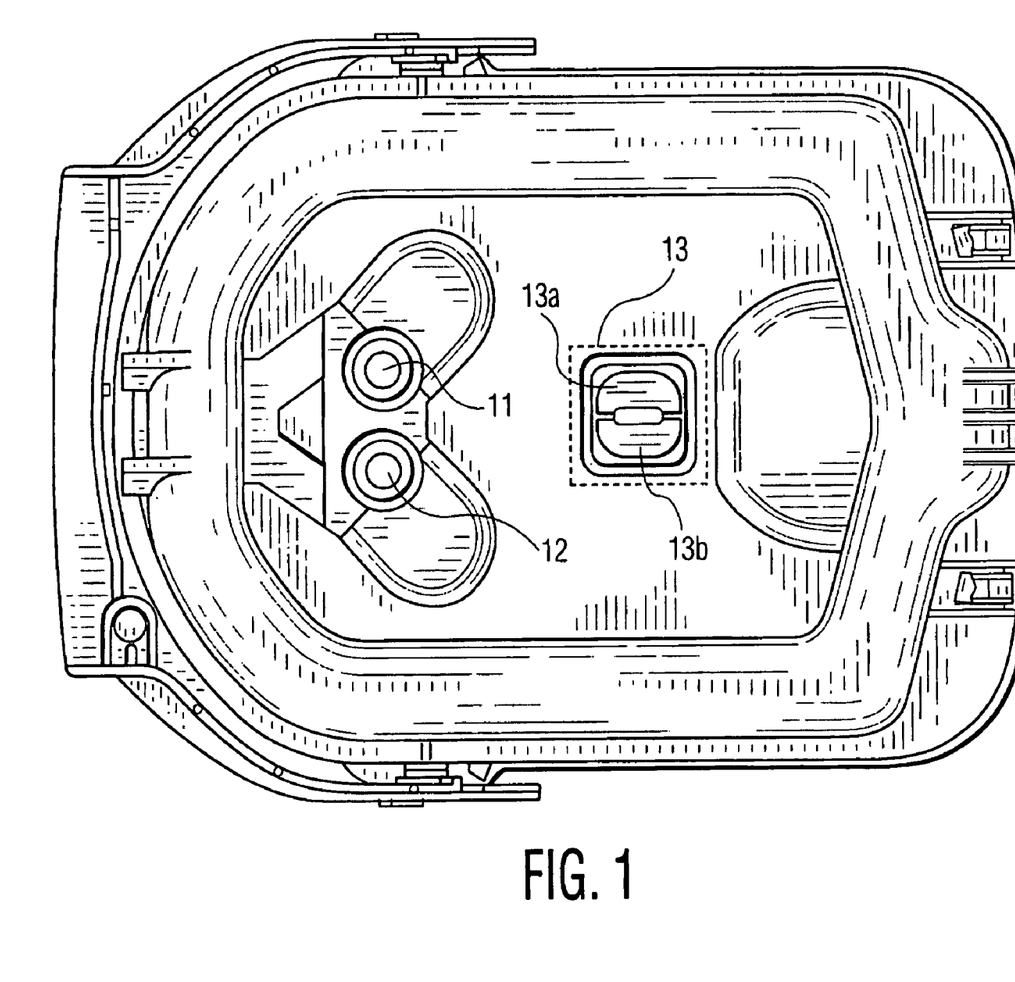
FIG. 1 illustrates an exemplary embodiment of an electrode package according to one aspect of the present invention.

In the embodiment 10 illustrated in FIG. 1, a shaped conductive label 13 having two portions 13a, 13b is disposed in the back of a rigid electrode cartridge 10. Contacts 11 and 12 are the power contacts through which the current or ECG signals flow when the electrodes are in use (of course, assuming the mode of operation requires current or ECG signal). The electrodes (not shown) are stored within the cartridge 10 and connect through the cartridge wall to the defibrillator (not shown). The electrode connections 11, 12 are separate from the conductive label 13.

Figure 4:
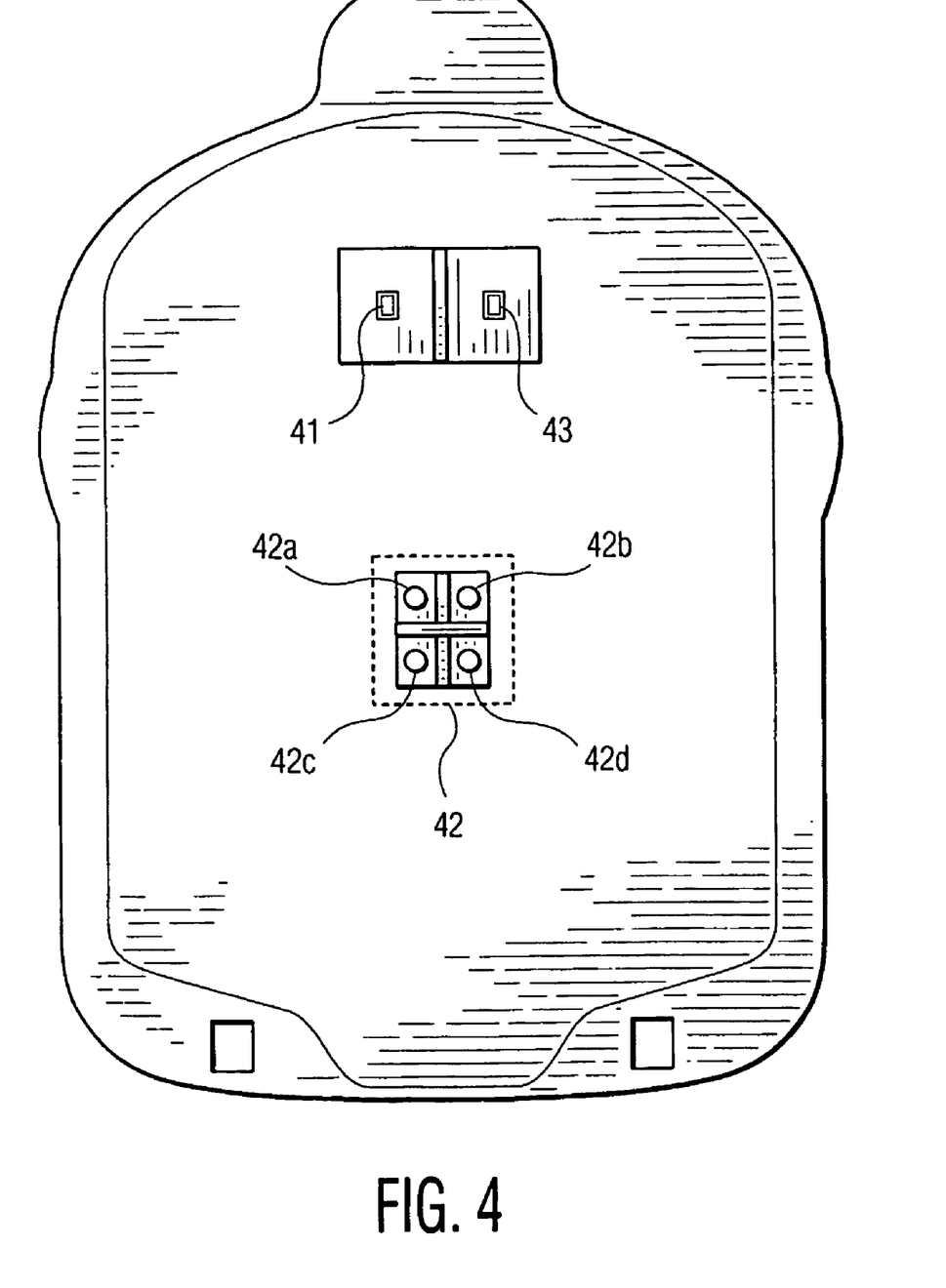
FIG. 4 illustrates an exemplary embodiment of an electrode receptacle for accepting one of the exemplary embodiments in FIGS. 1-3 according to still another aspect of the present invention.

Installation of the cartridge 10 into the defibrillator cartridge receptacle (see element 40, FIG. 4) places the portions 13a, 13b of the conductive label 13 in electrical contact with four spring-loaded pins (see element 42, FIG. 4) projecting from the receptacle 40. In this embodiment 40, the top two pins 42b, 42d contact the portion 13b of conductive label 13, and the bottom two pins 42a, 42c contact the portion 13a of conductive label 13. Thus, conductive label portion 13a electrically shorts pin 42a to pin 42c, and conductive label portion 13b shorts pin 42b to pin 42d. The AED senses the resultant combination of electrical shorts and matches the sensed combination to a known cartridge type. In general, the shape of the conductive label 13 can be altered such that some or all of the pins 42a-d are shorted together in a unique combination to connote the type of electrode cartridge 10 to which the conductive label 13 is applied. The sensing pins (42a-d) are disposed to couple in a unique pattern to two or more portions of each of the shaped metallic labels to redundantly identify the particular type of electrode.

The conductive label 13 is preferably a material that will not erode under vibration or corrode over time. Erosion or corrosion could cause the sensed label shape to change, by opening what was otherwise an intended electrical short path. Therefore, the preferred label material is a gold-plated metal foil. Alternatively, the label could be comprised of a metallized printed circuit board or of a solid metal plaque.

In addition, the defibrillator sensing pins 42 should be held under elastic compression against the label 13, when the cartridge 10, 20, 30 is installed. Such a disposition reduces erosive wear under vibration or shock, while maintaining a secure electrical connection. The compression device should be set low enough to prevent damage to the pins 42 during use. An exemplary embodiment of the elastic compression device includes a spring-loaded pin. Alternatively, the elastic compression device may be disposed between conductive label 13 and the electrode cartridge body, such that the conductive label 13 is held under elastic compression against fixed pins 42.

Figure 2:
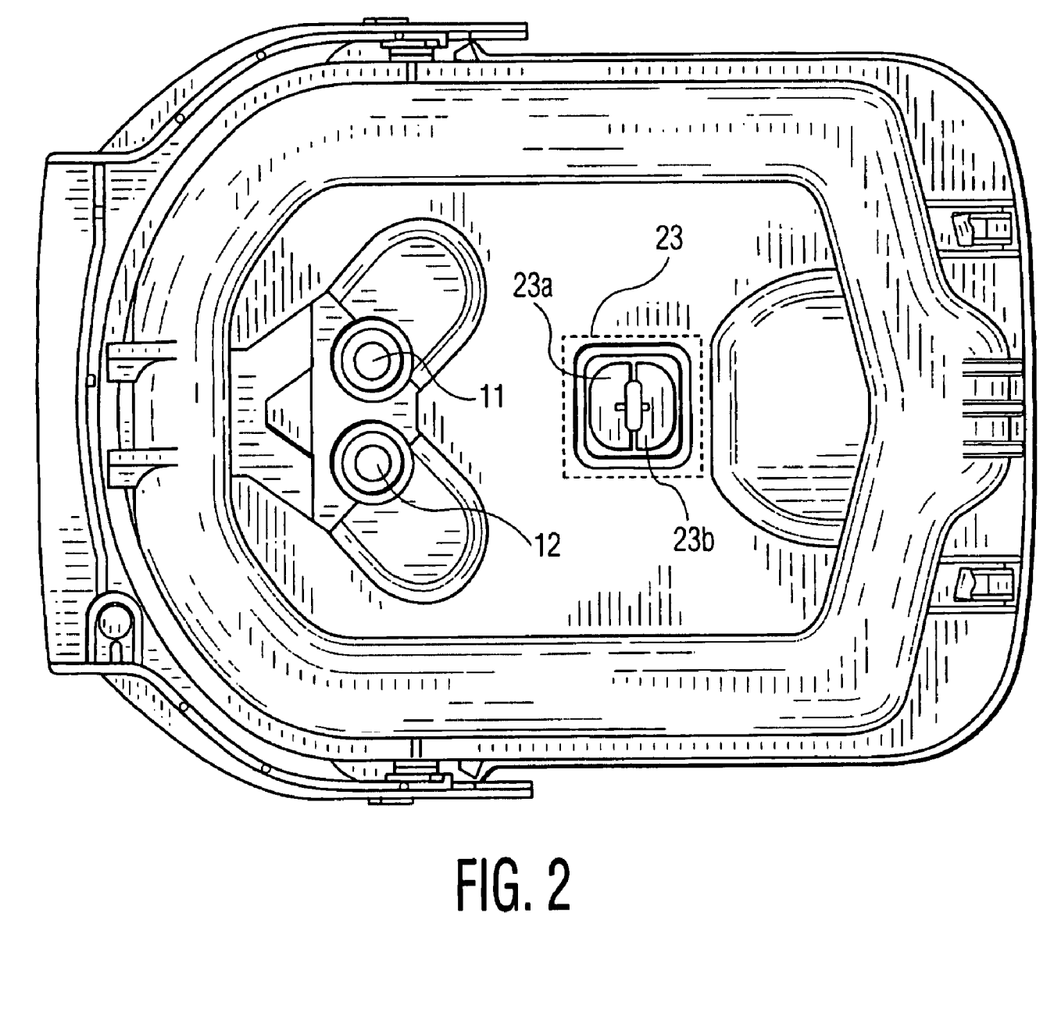
FIG. 2 illustrates another exemplary embodiment of an electrode package according to another aspect of the present invention.
Figure 3:
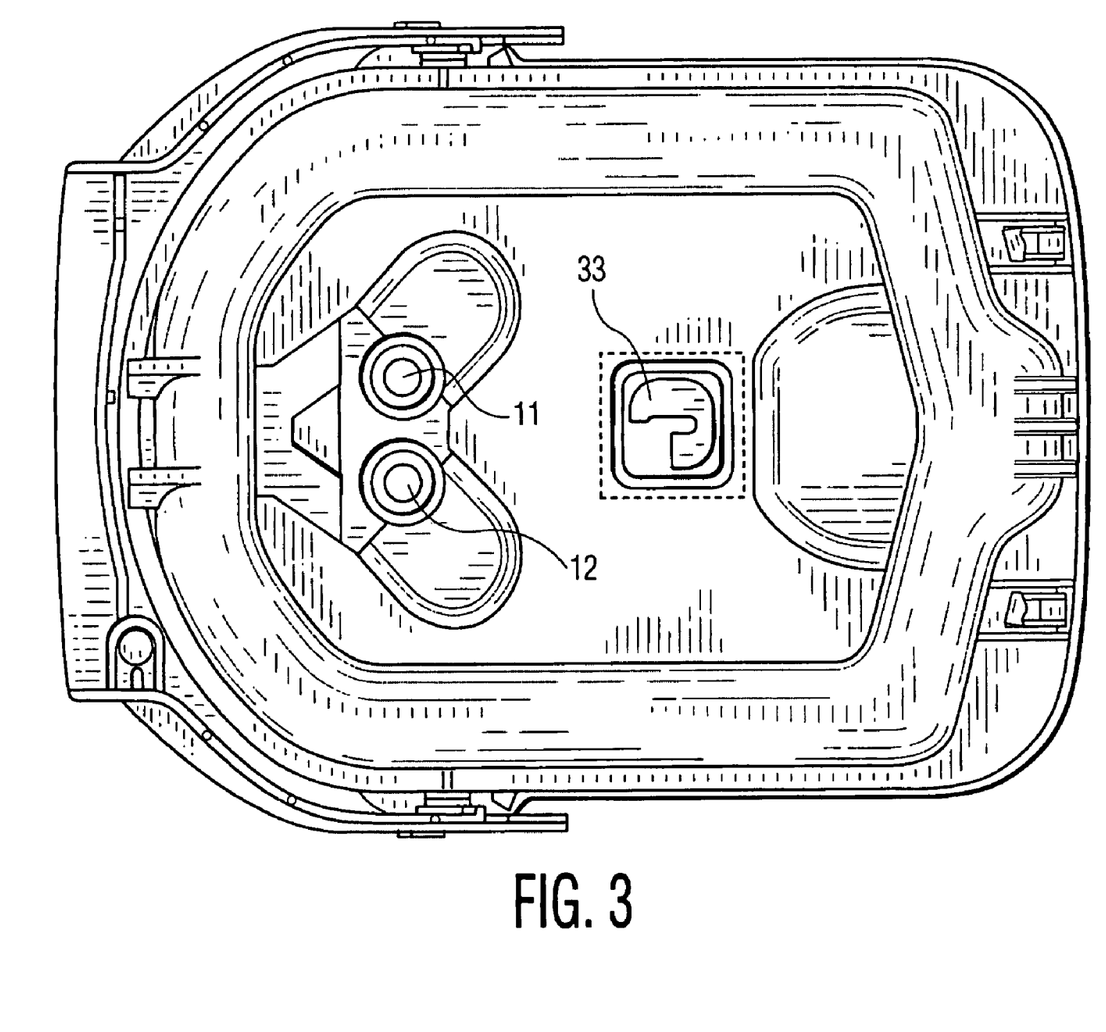
FIG. 3 illustrates another exemplary embodiment of an electrode package according to yet another aspect of the present invention.

The unique combination of connected pins 42, sensed by the defibrillator, indicates the type of electrode cartridge 10, 20, 30 installed. For example, a conductive label 13 for an adult electrode cartridge 10 may be a square with four quadrants, pairs of which are electrically conductive as shown in FIG. 1. Thus, pairs of sensing pins 42a-c and 42b-d are shorted. Certainly, this shape could be used for other types of electrodes (but not at the same time, of course), as long as the shape is uniquely matched to the type of electrode.

Turning to FIG. 2, shown therein is an exemplary embodiment 20 of another type of electrode cartridge. This can be used, for example, for a pediatric electrode cartridge. In this case, the conductive label 23 has two portions 23a, 23b that are rotated about 90 degrees relative to the conductive label 13 of FIG. 1. Thus, pins 42a and 42b contact portion 23a of conductive label 23 while pins 42b and 42c contact portion 23b of conductive label 23. This provides another unique combination of sensing pins to determine the type of electrode cartridge automatically.

Turning to FIG. 3, shown therein is an exemplary embodiment 30 of another type of electrode cartridge. This can be used, for example, for a training electrode cartridge. In this case, the conductive label 33 has a single portion. Thus, pins 42a, 42c and 42d contact conductive label 33 while pin 42b remains isolated. This provides another unique combination of sensing pins to determine the type of electrode cartridge automatically.

Figure 5:
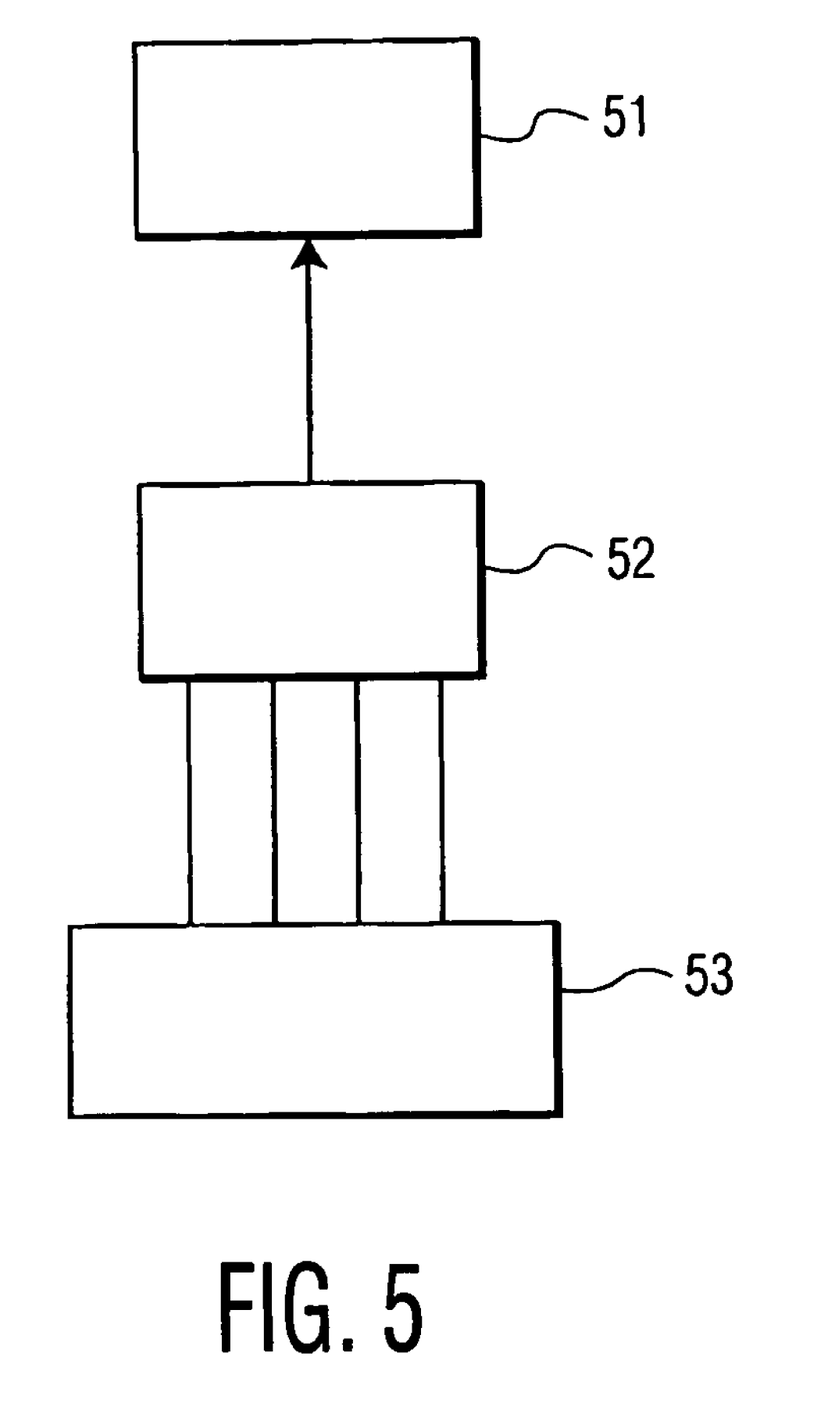
FIG. 5 depicts a block diagram of an exemplary embodiment of an automatic external defibrillator according to still another aspect of the present invention.

Turning to FIG. 5, shown therein is a block diagram of an exemplary embodiment of an automatic external defibrillator.

In this embodiment 50, a processor 51 establishes the mode of operation of the AED. The sensing pins 52 are coupled to the processor 51 and in combination sense a unique shape of a shaped or coded conductive label 53 that is disposed on each of the electrode packages.

Each electrode package for an automatic external defibrillator includes a cartridge for containing electrodes of a particular type and a shaped conductive label disposed on the cartridge. The shaped conductive label uniquely identifies the particular type of electrode contained therein via its shape.

The AED also includes an electrode cartridge receptacle to accept each of the electrode cartridges. The electrode cartridge receptacle includes one or more sensing pins to couple in a unique pattern to each of the shaped conductive labels when the electrode cartridge is inserted into the electrode cartridge receptacle.

The processor establishes a mode of operation of the automatic external defibrillator based on the particular shaped conductive label sensed by the one or more sensing pins. In a preferred embodiment, each of the sensing pins is spring-loaded to maintain the sensing pin in electrical contact with a portion of the shaped conductive label when the electrode cartridge is inserted into the electrode cartridge receptacle.

Each of the automatic external defibrillator electrode cartridges includes two contacts for interfacing the patient electrodes contained therein to the defibrillator and the automatic external defibrillator electrode cartridge receptacle includes two opposing contacts which mate with the two contacts on each of the automatic external defibrillator electrode cartridges. The two contacts on the automatic external defibrillator electrode cartridge receptacle are different than the sensing pins.

Other shapes than those shown herein will cause different combinations of the four sensing pins to be shorted or opened. There can be more sensing pins that four, as well as less sensing pins than four.

Figure 6:
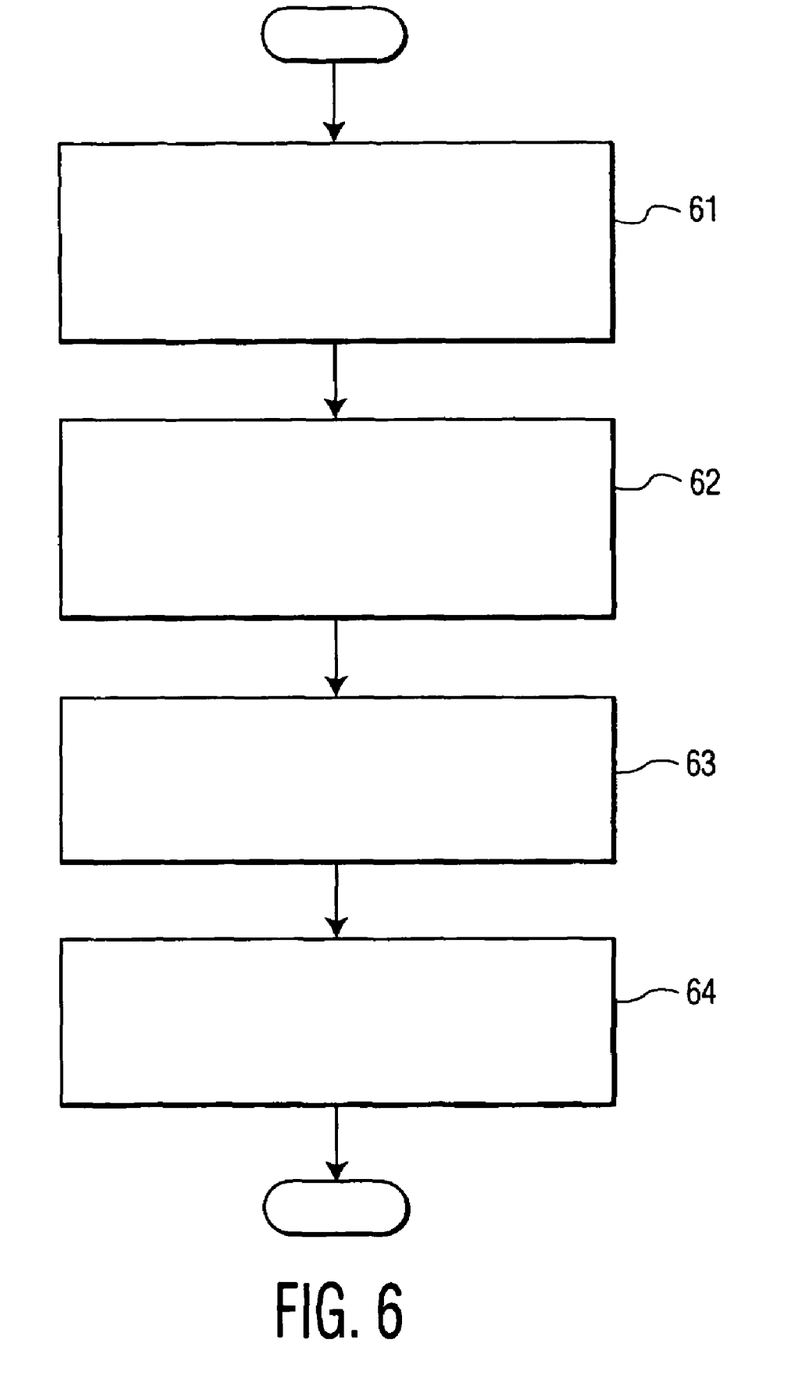
FIG. 6 depicts a flow chart of an exemplary embodiment of a method for identifying a type of electrode package in an automatic external defibrillator according to yet another aspect of the present invention.

Turning to FIG. 6, shown therein is an exemplary embodiment of a method 60 for identifying an electrode package in an AED and for operating the AED accordingly.

In step 61, a shaped conductive label is provided on an automatic external defibrillator electrode package that uniquely identifies a type of electrode contained therein. The shaped conductive label can be square, half-moon shaped, or any other unique shape for each type of electrode package that results in different combination of pins contacting the shaped conductive label.

In step 62, one or more pins are coupled to the shaped conductive label when the automatic external defibrillator electrode package is coupled to the defibrillator. Different combinations of pins will contact the shaped conductive label for different electrode types.

In step 63, the shape of the shaped conductive label is sensed with the one or more pins to ascertain the type of electrode contained therein. This can be accomplished by redundantly sensing two or more portions of the shape of the shaped conductive label with two or more pins to ascertain the type of electrode contained therein.

In step 64, an operating mode for the automatic external defibrillator is selected based on the shape of the shaped conductive label sensed by the combination of the pins. For example, if all four pins are contacted (shorted or opened), then one mode of operation is selected, whereas if only three pins are contacted (shorted or opened), another mode is selected.

There are a number of advantages to the present invention. First, because the electrode type identification system is separate from the defibrillation energy connector, a potential misidentification due to an incorrectly installed or dislodged connector is eliminated. Second, the defibrillator identification pins and the conductive label can be disposed for identification redundancy. For example, referring to the electrode cartridge 10 of FIG. 1 and the defibrillator pins 42a-d in FIG. 4, the defibrillator can be configured to positively identify the cartridge type based on detecting either of the shorted pin pairs 42b-d or 42a-c. In this embodiment, one broken pin or contact blocked by debris in one pin pair will not confuse the defibrillator because the other pin pair will be shorted and detected normally.

Not only can the conductive label be fabricated inexpensively, but also the label orientation by itself can connote a specific electrode type. Thus, a single label design can denote two or more cartridge types. FIGS. 1-3 illustrate one embodiment of the conductive label, although the label of an exemplary embodiment could be fabricated or applied under different orientations to identify at least twelve different electrode types.

Additionally, the label can be uniquely coded to indicate the type of electrode, which code is sensed by the electrode cartridge receptacle. For example, a bar code could be employed as a unique label.

Although various embodiments are specifically illustrated and described herein, it will be appreciated that modifications and variations of the invention are covered by the above teachings and are within the purview of the appended claims without departing from the spirit and intended scope of the invention. For example, specific shapes for the conductive labels are depicted herein, yet other shapes are possible without departing from the scope of the present invention. Substitute contact elements that function similarly to pins will be obvious to one of ordinary skill in the art. Moreover, while four pins are shown, other numbers of pins can be used without departing from the scope of the present invention. Furthermore, these examples should not be interpreted to limit the modifications and variations of the invention covered by the claims but are merely illustrative of possible variations.

The invention claimed is:

1. A method for identifying an electrode type in an automatic external defibrillator comprising the steps of:
providing on an automatic external defibrillator electrode package which includes an electrical connector for coupling an electrode to the defibrillator a shaped conductive label having a conductive path that uniquely identifies a type of electrode contained therein;
coupling the electrode electrical connector to an electrode connector of the defibrillator; and
coupling one or more conductors to the shaped conductive label when the automatic external defibrillator electrode package is coupled to the defibrillator.

2. The method according to claim 1, further comprising the step of:
sensing a shape of the shaped conductive label with the one or more conductors to ascertain the type of electrode contained therein.

3. The method according to claim 1, further comprising the step of:
selecting an operating mode for the automatic external defibrillator based on the shape of the shaped conductive label.

4. The method according to claim 2, wherein said sensing step further comprises redundantly sensing two or more portions of said shape of the shaped conductive label with two or more conductors to ascertain the type of electrode contained therein.

5. An electrode package for an automatic external defibrillator comprising:
a cartridge for containing one or more electrodes of a particular type; and
a shaped conductive label disposed on the cartridge, said shaped conductive label uniquely identifying the particular type of electrode contained therein via the shape of said shaped label.

6. An automatic external defibrillator comprising:
one or more electrode cartridges, each containing one or more electrodes of a particular type; and
one or more shaped conductive labels, each disposed on one of the one or more electrode cartridges, each of said one or more shaped conductive labels uniquely identifying a particular type of electrode contained therein based on the shape of said shaped label.

7. The automatic external defibrillator according to claim 6, further comprising:
an electrode cartridge receptacle to accept each of the one or more electrode cartridges, said electrode cartridge receptacle including one or more sensing pins to couple in a unique pattern to the one or more shaped conductive labels when each of the one or more electrode cartridges is inserted into the electrode cartridge receptacle.

8. The automatic external defibrillator according to claim 7, wherein said sensing pins are disposed to couple in a unique pattern to two or more portions of each of said shaped conductive labels to redundantly identify said particular type of electrode.

9. The automatic external defibrillator according to claim 7, further comprising:
a processor establishing a mode of operation of the automatic external defibrillator based on the particular one of the one or more shaped conductive labels sensed by the one or more sensing pins.

10. The automatic external defibrillator according to claim 7, wherein each of the one or more sensing pins comprises a spring-loaded pin to maintain said each sensing pin in electrical contact with the one or mode shaped conductive labels when each of the one or more electrode cartridges is inserted into the electrode cartridge receptacle.

11. The automatic external defibrillator according to claim 7, wherein each of the one or more shaped conductive labels comprises a gold-plated metal.

12. The automatic external defibrillator according to claim 9, wherein each of the one or more shaped conductive labels comprises a unique shape.

13. The automatic external defibrillator according to claim 12, wherein the one or more sensing pins sense the unique shape of the one or more shaped conductive labels when each of the one or more electrode cartridges is inserted into the electrode cartridge receptacle.

14. The automatic external defibrillator according to claim 13, wherein the processor establishes a mode of operation of the automatic external defibrillator based on the sensed shape of the conductive label.

15. The automatic external defibrillator according to claim 7, wherein each of the automatic external defibrillator electrode cartridges includes two contacts for electrically connecting patient electrodes to the automatic external defibrillator and the automatic external defibrillator electrode cartridge receptacle includes two contacts for electrically connecting the automatic external defibrillator to the two contacts on each of the automatic external defibrillator electrode cartridges, and said two contacts on the automatic external defibrillator electrode cartridge receptacle are different than said one or more sensing pins.

16. A method for identifying an electrode type in an automatic external defibrillator comprising the steps of:

provanding a first conductive label on a first type of an automatic external defibrillator electrode package, said first conductive label having a first shape that uniquely identifies a type of electrode contained therein; and providing a second conductive label on a second type of an automatic external defibrillator electrode package, said second conductive label having a second shape that uniquely identifies a type of electrode contained therein.

17. The method according to claim 16, further comprising the step of:

coupling one or more pins to the first or second conductive label when the automatic external defibrillator electrode package on which the first or second conductive label, respectively, is disposed is coupled to the defibrillator.

18. The method according to claim 17, wherein the one or more pins comprise one or more spring-loaded pins.

19. The method according to claim 17, further comprising the step of:

sensing a shape of the shaped conductive label with the one or more pins to ascertain a type of electrode contained therein.

20. The method according to claim 16, further comprising the step of:

selecting an operating mode for the automatic external defibrillator based on the shape of the first and second shaped conductive labels.

* * * * *